United States Patent [19]

Inoue et al.

[11] Patent Number: 5,834,288
[45] Date of Patent: Nov. 10, 1998

[54] **KDN-SPECIFIC DEMINONEURAMINIDASE FROM *SPHINGOBACTERIUM MULTIVORUM***

[75] Inventors: Yasuo Inoue; Sadako Inoue, both of Taipei, Taiwan; Ken Kitajima, Nagoya, Japan

[73] Assignee: Seikagaku Corporation, Tokyo, Japan

[21] Appl. No.: 765,491

[22] PCT Filed: Jun. 19, 1995

[86] PCT No.: PCT/JP95/01213

§ 371 Date: Apr. 8, 1997

§ 102(e) Date: Apr. 8, 1997

[87] PCT Pub. No.: WO96/00781

PCT Pub. Date: Jan. 11, 1996

[30] Foreign Application Priority Data

Jun. 28, 1994 [JP] Japan .................................. 6-146820

[51] Int. Cl.$^6$ ................................ C12N 9/26; C12N 9/24
[52] U.S. Cl. ............................................. 435/201; 435/200
[58] Field of Search ...................................... 435/200, 201

[56] References Cited

U.S. PATENT DOCUMENTS 5,449,615  9/1995  Li et al. ................................... 435/200

OTHER PUBLICATIONS

Ghosh et al. (1991) Anal. Biochem., 196 (1), "Use of Exoglycosidases from *Mercenaria mercenaria* (Hard Shelled Clam) as a Tool for Structural Studies of Glycosphingolipids and Glyocoproteins", pp. 252–261.

Li et al. (1994) Arch. Biochem. Biophys., 310 (1), "A Novel Sialidase Capable of Cleaving 3–Deoxy–D–glycero–D–galacto–2–nonulosonic Acid (KDN)", pp. 243–246.

Wilson et al. (1996) Glycoconj. J., 13 (6), "A $^1$H–NMR Investigation of the Hydrolysis of a Synthetic Substrate by KDN–Sialidase from *Crassostrea virginica*", pp. 927–931.

Nishino et al. (1996) J. Biol. Chem., 271 (6), "Induction, Localization, and Purification of a Novel Sialidase, Deaminoneuraminidase (KDNase), from *Sphingobacterium multivorum*", pp. 2909–2913.

Yuziuk et al. (1996) Biochem. J., 315 (3), "Two Different Sialidases, KDN–Sialidase and Regular Sialidase in the Starfish *Asterina pectinifera*", pp. 1041–1048.

Kitajima et al. (1994) J. Biol. Chem., 269 (34), "Discovery of a New Type of Sialidase, KDNase, Which Specifically Hydrolyzes Deaminoneuraminyl (3–Deoxy–D–glycero–D–galacto–2–nonulosonic Acid) but not N–Acylneuraminyl Linkages", pp. 21415–21419.

*Primary Examiner*—Jon P. Weber
*Attorney, Agent, or Firm*—Knobbe, Martens, Olson & Bear, LLP

[57] ABSTRACT

The bacterium *Sphingobacterium multivorum* has been cultivated to produce a deaminoneuraminidase which is specific for catalyzing the hydrolysis of the ketosidic linkage formed by deaminoneuraminic acid in complex carbohydrates. The deaminoneuraminidase does not catalyze the hydrolysis of either the ketosidic linkage formed by N-acetylneuraminic acid or the ketosidic linkage formed by n-glycolylneuraminic acid and complex carbohydrates.

5 Claims, 10 Drawing Sheets

KDN-SPECIFIC DEMINONEURAMINIDASE FROM *SPHINGOBACTERIUM MULTIVORUM*

TECHNICAL FIELD

The present invention relates to a novel deaminoneuraminidase. In particular, the present invention relates to a deaminoneuraminidase having no sialidase activity.

BACKGROUND ART

Deaminoneuraminic acid (3-deoxy-D-glycero-D-galacto-nonulosonic acid or 2-keto-3-deoxy-D-glycero-D-galacto-nononic acid; hereinafter referred to as "KDN") has the same structure as that of sialic acid except that N-acyl group linked to 5-position carbon of sialic acid is replaced with hydroxyl group. It has been heretofore revealed that KDN widely ranges over the living world, as a constitutional component of complex carbohydrate, and has a variety of existing forms, in the same manner as sialic acid. On the other hand, KDN has unique properties different from those of sialic acid. For example, it has been clarified that KDN-containing complex carbohydrate plays an important role in the ovum-sperm interaction during fertilization. A great interest is attracted by elucidation of structure and function of KDN-containing glycoprotein and glycolipid.

By the way, those known as an enzyme to cleave the KDN ketosidic linkage of KDN-containing complex carbohydrate (deaminoneuraminidase; hereinafter referred to as "KDNase", if necessary) include KDN-sialidase existing in liver of loach (Li, Y. -T. et al. *Archives of Biochemistry and Biophysics,* Vol. 310, No. 1, pp. 243–246 (1994)). The present inventors have found that an enzyme having a sialidase activity and a deaminoneuraminidase activity exists in a tissue such as ovary of fish such as rainbow trout (Angata, T. et al., *Glycobiology,* Vol. 4, pp. 517–523 (1994)).

However, any of the foregoing enzymes does not specifically cleave the KDN ketosidic linkage. Some of the foregoing enzymes involve a sialidase activity to a degree approximately the same as the activity to cleave the KDN ketosidic linkage (enzyme originating from loach described above), and others involve a sialidase activity stronger than the activity to cleave the KDN ketosidic linkage (enzyme originating from rainbow trout described above). No enzyme has been known, which specifically acts on only KDN. The enzyme originating from loach is known to have an optimum pH of about 4.5. The present inventors have found that the enzyme originating from rainbow trout has an optimum pH of about 4.4.

It is known that the enzyme originating from loach has, in the vicinity of pH 6, an amount of the deaminoneuraminidase activity which is 65% of an amount of the deaminoneuraminidase activity obtained at its optimum pH. On the other hand, the present inventors have found that no deaminoneuraminidase activity is found in the vicinity of pH 6.5 in the case of the enzyme originating from rainbow trout. Therefore, it has been difficult to make a deaminoneuraminidase reaction under a condition of neutral pH. Further, any of the foregoing deaminoneuraminidases is an enzyme which originates from the animal. No deaminoneuraminidase has been known at all, which originates from any microorganism. Accordingly, an obtainable amount of the enzyme has been also limited.

DISCLOSURE OF THE INVENTION

It is expected that a deaminoneuraminidase, if any, which has a high activity and is active in a neutral pH range, may be extremely useful for studies such as analysis of structure and function of deaminoneuraminic acid. If a deaminoneuraminidase having a high activity is obtained, it is expected to create, for example, new deaminoneuraminic acid-containing complex carbohydrates or carbohydrates by allowing such an enzyme to perform a reverse reaction of hydrolysis of the KDN ketosidic linkage.

The present invention has been made taking the foregoing viewpoints into consideration, an object of which is to provide a KDNase that is extremely specific to the KDN ketosidic linkage, having a high KDNase activity even in a neutral region, and not acting on any N-acylneuraminic acid residue, unlike the hitherto known sialidases having some KDNase activity.

In order to achieve the object described above, the present inventors diligently screened out microorganisms which produced KDNases. As a result, the present inventors have found out that a bacterial species belonging to the genus Sphingobacterium produces a KDNase. Further, the present inventors have found out that the KDNase has a high activity in a neutral region, and does not exhibit any sialidase activity. Thus the present invention has been completed.

Namely, the present invention lies in a deaminoneuraminidase having the following enzymological properties:

(1) action:
the deaminoneuraminidase acts on complex carbohydrate or carbohydrate containing deaminoneuraminic acid, and hydrolyzes ketosidic linkage formed by deaminoneuraminic acid to produce free deaminoneuraminic acid and complex carbohydrate or carbohydrate containing no deaminoneuraminic acid, or complex carbohydrate or carbohydrate from which deaminoneuraminic acid is partially removed;

(2) substrate specificity:
the deaminoneuraminidase acts on complex carbohydrate or carbohydrate containing deaminoneuraminic acid, but does not act on ketosidic linkage formed by N-acetylneuraminic acid or N-glycolylneuraminic acid in complex carbohydrate or carbohydrate containing N-acetylneuraminic acid or N-glycolylneuraminic acid.

In a specified embodiment of the present invention, the deaminoneuraminidase of the present invention further has the following physicochemical properties:

(i) optimum reaction pH:
the deaminoneuraminidase has an optimum reaction pH in the vicinity of pH 6;

(ii) stable pH range:
the deaminoneuraminidase is stable in a range of pH 4 to 9 at 25° C.;

(iii) optimum reaction temperature:
the deaminoneuraminidase has an optimum reaction temperature in the vicinity of 25° C.;

(iv) thermal stability:
the deaminoneuraminidase is not inactivated at 25° C. for at least 48 hours;

(v) inhibition and stabilization:
the deaminoneuraminidase is inhibited by free deaminoneuraminic acid, and the deaminoneuraminidase is stabilized in the presence of protein such as bovine serum albumin.

In a preferred embodiment, the present invention lies in the deaminoneuraminidase having the foregoing properties, produced by Sphingobacterium mOL12-4s.

In another aspect, the present invention provides a method for producing deaminoneuraminidase, comprising the steps of cultivating a bacterium which belongs to the genus Sphingobacterium and has a deaminoneuraminidase-producing ability, and collecting, from an obtained culture, the deaminoneuraminidase having the foregoing properties. In still another aspect, the present invention provides Sphingobacterium mOL12-4s having a deaminoneuraminidase-producing ability.

In still another aspect, the present invention provides a method for producing carbohydrate and/or complex carbohydrate containing deaminoneuraminic acid, comprising the step of allowing the deaminoneuraminidase having the foregoing properties to coexist with deaminoneuraminic acid and carbohydrate and/or complex carbohydrate.

The KDNase of the present invention is occasionally referred to as "enzyme of the present invention", if necessary. The term "complex carbohydrate or carbohydrate containing KDN" refers to those in which KDN is linked through ketosidic linkage to complex carbohydrate such as glycoprotein and glycolipid, or carbohydrate such as monosaccharide, oligosaccharide, and polysaccharide. The term "complex carbohydrate or carbohydrate containing sialic acid (including N-acetylneuraminic acid and N-glycolylneuraminic acid)" refers to those in which sialic acid is linked through ketosidic linkage to complex carbohydrate or carbohydrate. The term "sialidase activity" herein refers to an activity to degrade ketosidic linkage formed by sialic acid in complex carbohydrate or carbohydrate containing sialic acid, which does not include the KDNase activity possessed by the hitherto known sialidases.

The present invention will be explained in detail below.

<1> KDNase of the Present Invention
(1) Method for preparing the enzyme of the present invention The deaminoneuraminidase of the present invention is a novel enzyme having the foregoing properties. The enzyme of the present invention can be prepared, for example, by cultivating a bacterium belonging to the genus Sphingobacterium, and collecting the enzyme from an obtained culture of the bacterium. The bacterium belonging to the genus Sphingobacterium is exemplified by *Sphingobacterium multivorum,* and it is specifically exemplified by Sphingobacterium mOL12-4s separated in accordance with the present invention.

Specifically, an enzyme sample having a desired degree of purification can be collected as follows. Namely, a microorganism, which produces the enzyme of the present invention, is inoculated into an appropriate medium to perform cultivation. Microbial cells are collected from a culture (or a culture liquid in the case of cultivation in liquid) obtained after the cultivation by means of, for example, centrifugation. The microbial cells are disrupted by means of, for example, an ultrasonic treatment to obtain a cell-disrupted solution. Alternatively, for example, a fraction is obtained from the microbial cells by means of osmotic shock, which has the enzyme activity released to the outside of the microbial cells. After that, the cell-disrupted solution or the fraction obtained by the osmotic shock is used as a starting material to which general methods for separating the enzyme are applied by using the KDNase activity as an index.

The microorganism, which produces the enzyme of the present invention, can be cultivated at a temperature suitable for growth of the microorganism for a period of time ranging from several hours to several days in accordance with an aerobic cultivation method (for example, cultivation with shaking, and cultivation with aeration and agitation) in a medium containing, for example, a carbon source (including, for example, oligosaccharides containing KDN and glucose) which can be assimilated by the microorganism, a nitrogen source (including organic nitrogen sources such as yeast extract, peptone, meat extract, corn steep liquor, soybean meal, and casein hydrolysate (casamino acids); and inorganic nitrogen sources such as ammonium hydrochloride, ammonium sulfate, urea, and ammonium nitrate), and inorganic salts (including, for example, sulfate salts, phosphate salts, and hydrochlorides of calcium, magnesium, potassium, and sodium).

When the medium is added with KDN or a substance having the KDN ketosidic linkage such as KDN-containing oligosaccharide alcohol (hereinafter referred to as "KDN oligosaccharide alcohol", if necessary), then the KDNase is induced, and the enzyme activity per a unit number of microbial cells is increased. Accordingly, the enzyme of the present invention can be efficiently produced by the microorganism which produces the enzyme of the present invention. This effect is obtained more remarkably when the substance having the KDN ketosidic linkage such as KDN oligosaccharide alcohol is added to the medium than when KDN is added to the medium. It is not necessarily indispensable that the substance having the KDN ketosidic linkage such as KDN oligosaccharide alcohol to be added to the medium should be pure. It is also allowable to use, for example, a crudely purified preparation.

The microbial cells collected from the culture are disrupted by means of, for example, an ultrasonic treatment, or treated with an appropriate method such as osmotic shock to prepare a fraction containing the released enzyme, from which an enzyme sample having an objective degree of purification can be obtained by means of known methods for purifying the enzyme, including, for example, salting out by using, for example, ammonium sulfate $((NH_4)_2SO_4)$ or sodium sulfate; dialysis; ultrafiltration; adsorption chromatography; anion exchange chromatography; cation exchange chromatography; hydrophobic chromatography; gel filtration; and electrophoresis; as well as affinity chromatography by using, for example, agarose gel with KDN-containing glycoprotein (KDN-gp) linked thereto.

The KDNase activity of the enzyme of the present invention can be measured by allowing the enzyme of the present invention to act on, for example, complex carbohydrate or carbohydrate containing KDN, hydrolyzing the ketosidic linkage formed by KDN, and quantitatively measuring liberated KDN. Specifically, the following method is exemplified. Namely, the enzyme of the present invention is allowed to act on 4-methylumbelliferyl KDN (4-MU-KDN) to measure fluorescence of 4-methylumbelliferone liberated by enzymatic hydrolysis of the ketosidic linkage. Alternatively, the KDNase activity can be also measured by using, for example, a substrate of KDN-containing glycoprotein originating from ovarian liquid of rainbow trout, adding the enzyme of the present invention thereto to make a reaction, adding cetylpyridinium chloride (CPC) to an obtained reaction solution, obtaining a supernatant by means of centrifugation, and quantitatively measuring an amount of KDN in the supernatant in accordance with the thiobarbituric acid method (*Analytical Biochemistry,* Vol. 205, pp. 244–250 (1992)). The KDN-containing glycoprotein forms a complex in the presence of CPC and precipitates, while KDN liberated by the enzyme reaction does not precipitate. Accordingly, unreacted KDN-containing glycoprotein can be removed from the reaction system by means of centrifugation. The foregoing methods will be explained more specifically in Examples described later on.

(2) Physicochemical Properties of the enzyme of the present invention

The enzyme of the present invention is represented by the KDNase produced by Sphingobacterium mOL12-4s, which exhibits the following physicochemical properties.

1) Action

The enzyme of the present invention acts on complex carbohydrate or carbohydrate containing KDN, and hydrolyzes linkage between KDN and complex carbohydrate or carbohydrate linked thereto to produce free KDN and complex carbohydrate or carbohydrate having no KDN, or complex carbohydrate or carbohydrate from which KDN is partially removed. It has been confirmed that the enzyme of the present invention can also act on ketosidic linkage between KDN and a compound other than complex carbohydrate and carbohydrate, such as those in 4-methylumbelliferyl KDN.

As a result of the action of the enzyme of the present invention on a mixed solution of KDN and lactose, it has been found that a KDN-containing oligosaccharide chain is present in a reaction solution. Thus it has been confirmed that the enzyme of the present invention also catalyzes a reverse reaction of the reaction described above. Utilization of the reverse reaction makes it possible to produce KDN-containing carbohydrate and/or complex carbohydrate or the like by allowing the enzyme of the present invention to coexist with KDN and carbohydrate and/or complex carbohydrate or the like.

2) Substrate specificity

The enzyme of the present invention acts on and cleaves ketosidic linkage formed by deaminoneuraminic acid (KDN), but does not act on ketosidic linkage formed by N-acetylneuraminic acid or N-glycolylneuraminic acid.

The enzyme of the present invention cleaves all KDN residues existing in the following KDN-containing complex carbohydrates or carbohydrates or the like. The enzyme of the present invention acts on any of linkage forms known in the nature concerning KDN residues, i.e., ketosidic linkages of $\alpha2 \rightarrow 3$, $\alpha2 \rightarrow 6$, and $\alpha2 \rightarrow 8$:

(a) KDN-containing glycoprotein: mucin-like glycoprotein linked to a large number of sugar chains having three different types of KDN linkages (KDN$\alpha2 \rightarrow$3Gal, KDN$\alpha2 \rightarrow$8KDN, and KDN$\alpha2 \rightarrow$6GalNAc);

(b) KDN oligosaccharide alcohol obtained by treating KDN-containing glycoprotein with alkali-borohydride: general formula:

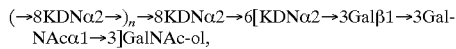

wherein n is 2 to 9, with an average of 5;

(c) KDN dimer, KDN$\alpha2 \rightarrow$8KDN;

(d) N-type sugar chain having two KDN residues linked through $\alpha2 \rightarrow$3Gal:

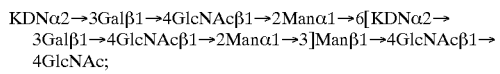

(e) sphingoglycolipid having KDN, KDN-containing ganglioside GM3: KDN$\alpha2 \rightarrow$3Gal$\beta1 \rightarrow$4Glc$\beta1 \rightarrow$Cer; and (f) 4-methylumbelliferyl KDN.

On the other hand, the enzyme of the present invention does not catalyze hydrolysis of ketosidic linkage formed by sialic acid in the known complex carbohydrate or carbohydrate containing sialic acid (N-acetylneuraminic acid and N-glycolylneuraminic acid) (see Example 2 described later on). Accordingly, the enzyme of the present invention is extremely highly specific to the ketosidic linkage formed by deaminoneuraminic acid.

3) Optimum reaction pH

The highest activity of the enzyme of the present invention is obtained in the vicinity of pH 6.

As illustrated in Example 2 described later on, an affinity-purified enzyme fraction of the enzyme of the present invention is obtained by purification by using column chromatography of Sephacryl S-200 (produced by Pharmacia) twice, and column chromatography of agarose gel (Affi-gel 15, produced by Bio Rad) with KDN-containing glycoprotein (KDN-gp) linked thereto, starting from a fraction obtained by precipitating, with 50–70% ammonium sulfate, a supernatant of a cell-disrupted solution of Sphingobacterium mOL12-4s. The relationship between pH and the enzyme activity, obtained by using the affinity-purified enzyme fraction, is shown in FIG. 8. As illustrated in Example 2 described later on, an enzyme sample, which is obtained by purification to give a single band on SDS-polyacrylamide gel electrophoresis (hereinafter referred to as "single purified enzyme", if necessary), is obtained by purification by successively performing column chromatography steps by using CM-Toyopearl 650M (produced by Toyo Soda), DEAE-Toyopearl 650M (produced by Toyo Soda), and CM-Toyopearl 650M (produced by Toyo Soda), starting from a fraction obtained by precipitating, with 90% ammonium sulfate, a supernatant of a cell-disrupted solution of Sphingobacterium mOL12-4s. The relationship between pH and the enzyme activity, obtained by using the single purified enzyme, is shown in FIG. 9.

4) Optimum reaction temperature

As for the enzyme of the present invention, a high enzyme activity is obtained in the vicinity of 25° to 30° C.

5) Stability

The enzyme of the present invention is relatively stable after being left to stand for several hours at 25° C. at pH 4 to 9. The enzyme of the present invention is not inactivated for at least 48 hours at 25° C. However, the enzyme of the present invention is unstable at a concentration of several tens of $\mu$g/ml or less, regardless of pH and ionic strength, while the enzyme of the present invention is stabilized in the presence of protein such as bovine serum albumin.

6) Inhibition and activation

The activity of the enzyme of the present invention is not affected by 1 mM of calcium ion ($Ca^{2+}$), magnesium ion ($Mg^{2+}$), manganese ion ($Mn^{2+}$), and EDTA (sodium ethylenediaminetetraacetic acid) respectively.

The activity of the enzyme of the present invention quickly increases as the ionic strength increases. In the case of NaCl, a maximum value is obtained in the presence of 300 mM NaCl, while the activity is extremely low at a low ionic strength of 50 mM or less.

The enzyme of the present invention is inhibited by free KDN (at a concentration of 3 mM). On the other hand, the enzyme of the present invention is not inhibited by free sialic acid which is a structural analog of deaminoneuraminic acid (KDN), and complex carbohydrate or carbohydrate having N-acetylneuraminic acid or N-glycolylneuraminic acid which does not serve as a substrate of the enzyme of the present invention. The enzyme of the present invention is not inhibited by 2,3-dehydro-2-deoxy-N-acetylneuraminic acid which is a specific inhibitor for known sialidase which cleaves the ketosidic linkage formed by N-acylneuraminic acid.

Triton X-100, which is a surfactant, does not inhibit the enzyme activity of the enzyme of the present invention. The enzyme activity of the enzyme of the present invention disappears in the presence of 0.5% sodium cholate, however, about 90% of the enzyme activity is maintained in the presence of 0.1% sodium cholate. According to this fact, when the enzyme of the present invention is allowed to act on KDN-containing glycolipid such as KDN-containing ganglioside, it is possible to add, for example, Triton X-100.

7) Molecular weight

As illustrated in Example 2 described later on, the molecular weight of the enzyme of the present invention is estimated to be about 50,000 based on gel filtration (Sephacryl S-200 column, 1.8 cm×135 cm; eluted with 20 mM Tris-HCl buffer (pH 8.0)/0.5M NaCl), or about 57,000 based on SDS-polyacrylamide gel electrophoresis, concerning an affinity-purified enzyme fraction of the enzyme of the present invention obtained by purification by using column chromatography of Sephacryl S-200 (produced by Pharmacia) twice, and column chromatography of agarose gel (Affi-gel 15, produced by Bio Rad) with KDN-containing glycoprotein (KDN-gp) linked thereto, starting from a fraction obtained by precipitating, with 50–70% ammonium sulfate, a supernatant of a cell-disrupted solution of Sphingobacterium mOL12-4s.

As illustrated in Example 2 described later on, the molecular weight of the enzyme of the present invention is estimated to be about 40,000 based on gel filtration (Sephacryl S-200 column, 1.8 cm×135 cm; eluted with 20 mM Tris-HCl buffer (pH 8.0)/0.2M NaCl), or about 42,000 based on SDS-polyacrylamide gel electrophoresis, concerning a single purified enzyme obtained by purification by successively performing column chromatography steps by using CM-Toyopearl 650M (produced by Toyo Soda), DEAE-Toyopearl 650M (produced by Toyo Soda), and CM-Toyopearl 650M (produced by Toyo Soda), starting from a fraction obtained by precipitating, with 90% ammonium sulfate, a periplasm (peripheral cytoplasm) liquid preparation seeped out from microbial cells of Sphingobacterium mOL12-4s by means of an osmotic shock method according to a method of Nossal and Heppel (*J. Biol. Chem.*, Vol. 241, pp. 3055 to 3062 (1966), however, the operation to obtain a supernatant by centrifugation after a treatment with 1 mM $Mg(CH_3COO)_2$ for 10 minutes is changed such that a supernatant is obtained by centrifugation after adding two volumes of 1M NaCl-1M Tris-HCl (pH 7.1) after the treatment with 1 mM $Mg(CH_3COO)_2$ for 10 minutes).

8) Michaelis constant

The Michaelis constant (Km) and the maximum enzyme reaction velocity (Vmax) of the enzyme of the present invention are as follows, as obtained when 4-methylumbelliferyl KDN (4-MU-KDN) is used as a substrate.

Km: 19 μM

Vmax: 0.19 μM/min or 7.4 mM/min/mg protein

9) Amino acid composition

The enzyme of the present invention has the following amino acid composition. Numerical values represent mole %.

|   |   |
|---|---|
| asparagine and aspartic acid | 5.3 |
| glutamine and glutamic acid | 5.5 |
| serine | 13.6 |
| glycine | 19.8 |
| histidine | 2.0 |
| arginine | 2.0 |
| threonine | 6.7 |
| alanine | 9.0 |
| proline | 3.5 |

-continued

|   |   |
|---|---|
| tyrosine | 5.6 |
| valine | 5.9 |
| methionine | 7.6 |
| isoleucine | 3.5 |
| leucine | 4.9 |
| phenylalanine | 3.2 |
| lysine | 2.0 |

<2> Sphingobacterium mOL12-4s of the Present Invention

The microorganism of the present invention, i.e., Sphingobacterium mOL12-4s was obtained by performing cultivation in an enrichment medium comprising a sole carbon source of oligosaccharide alcohol containing deaminoneuraminic acid (KDN) starting from sludge obtained in a fish farm, and selecting a microorganism having an activity to hydrolyze 4-MU-KDN in its cell-disrupted solution. The microorganism of the present invention is characterized in that it produces the KDNase described above having no sialidase activity.

In the same manner as described above, the microorganism of the present invention can be also obtained by performing cultivation in an enrichment medium comprising a sole carbon source of KDN-containing complex carbohydrate or carbohydrate or the like starting from soil or sludge obtained in a fish farm or the like, and performing screening by using an index whether or not the KDNase activity is exhibited. It is noted that Sphingobacterium mOL12-4s separated in accordance with the present invention has been deposited on May 24, 1994 in National Institute of Bioscience and Human Technology of Agency of Industrial Science and Technology of Ministry of International Trade and Industry, 1-3, Higashi 1-chome, Tsukuba-shi, Ibaraki-ken, 305 Japan, under a deposition number of FERM P-14325, transferred to international deposition based on the Budapest Treaty on May 26, 1995, and deposited under a deposition number of FERM BP-5116.

The microorganism of the present invention has its microbiological features as demonstrated in Example 1 described later on. The microorganism of the present invention has been identified to be a bacterium belonging to the genus Sphingobacterium according to its properties. This microorganism is highly possibly *Sphingobacterium multivorum.*

BEST MODE FOR CARRYING OUT THE INVENTION

Figure 1:
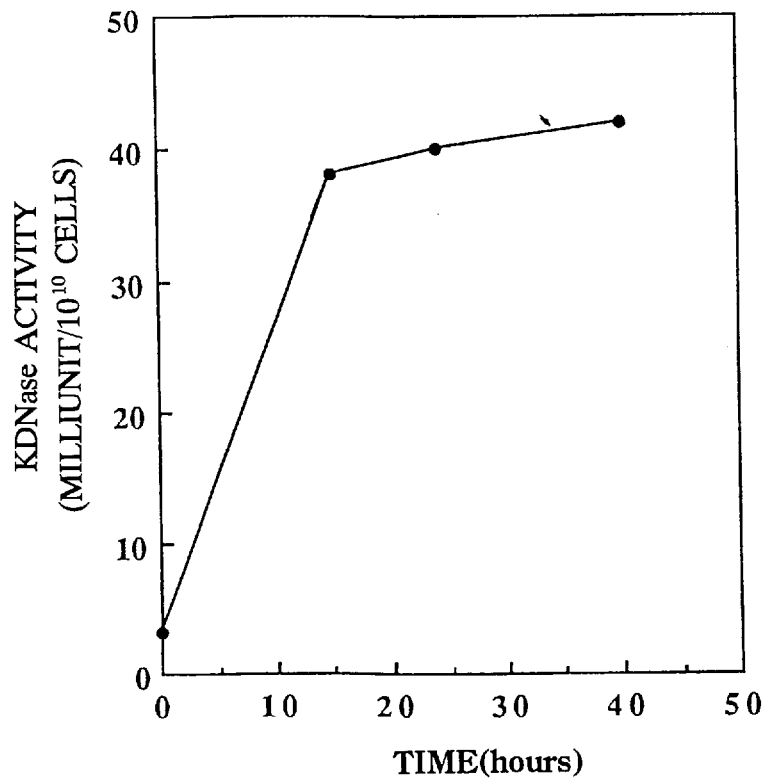
FIG. 1 shows a result of measurement performed along with passage of time for the KDNase activity per a number ($10^{10}$) of microbial cells, obtained by cultivation of Sphingobacterium mOL12-4s in a medium added with 0.1% crude KDN-OS (fraction prepared from rainbow trout, rich in KDN oligosaccharide alcohol (KDNα2→3Galβ1→3GalNAcα1→3[KDNα2→(8KDNα2→)$_n$→6]GalNacol, wherein n=5)).

The present invention will be explained more specifically below with reference to Examples. However, Examples are only illustrative of the present invention, and there is no limitation thereto. In Examples, the KDNase activity was measured in accordance with the following method.

<Method for Measuring Enzyme Activity>
(1) Method based on the use of 4-methylumbelliferyl KDN (4-MU-KDN method)

When the ketosidic linkage of 4-methylumbelliferyl KDN (4-MU-KDN) is enzymatically hydrolyzed as represented by the following reaction scheme, fluorescent 4-methylumbelliferone is liberated. Fluorescence thus obtained is measured.

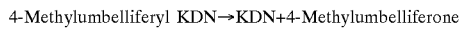

4-Methylumbelliferyl KDN→KDN+4-Methylumbelliferone

Specifically, 1.4 nmol of 4-MU-KDN was added to an enzyme solution prepared by dissolving the enzyme in 20 μl of 0.1M Tris-acetate buffer (pH 6.0)/0.1M NaCl to perform a reaction at 25° C. for 30 minutes. After the reaction, an aliquot of the reaction solution (20 μl) was mixed with 2.5 ml of 85 mM glycine-carbonate buffer (pH 9.3) to measure the fluorescent strength (exciting wavelength: 365 nm, measuring wavelength: 450 nm). For the measurement of the fluorescent strength, reference was made to *Biochemistry*, Vol. 18, No. 13, pp. 2783–2787. A fluorescent strength, which was obtained when the reaction was performed in the same manner as described above except that the enzyme was not added, was used as control. An amount of the enzyme, which hydrolyzed 1 nmol of 4-MU-KDN per 1 minute at 25° C., was defined as 1 unit.

4-MU-KDN used in this method was obtained in accordance with a method developed by Dr. Thomas G. Warner as described below. 4-MU-KDN used in this method was kindly given by Dr. Thomas G. Warner.

KDN was enzymatically synthesized from D-mannose and pyruvic acid by using Neu5Ac aldolase in accordance with a known method [Auge, C. et al., *Tetrahedron*, 46, 201–214 (1990)]. KDN was dried, and then it was suspended in 10 ml of acetic anhydride and 10 ml of pyridine, followed by a reaction at room temperature overnight. The reaction solution was cooled with ice. The reaction was stopped by adding methanol, and the solvent was removed. The residue was dissolved in methanol, which was applied to a Dowex 50 ($H^+$) column (4×5 cm), followed by elution with methanol. After removing the solvent, the eluted material was added with an excessive amount of diazomethane in ethyl ether to produce methyl ester. The produced completely acetylated methyl ester was applied to a silicic acid column (2.5×17 cm), followed by elution with a concentration gradient of ethyl acetate in hexane to obtain methyl-2, 4,5,7,8,9-hexa-O-acetyl KDN (K1). After that, K1 was converted into glycosyl chloride in accordance with a known method [Warner et al., *Biochemistry*, 18, 2783–2787 (1979)] to make a reaction with a sodium salt of 4-methylumbelliferone (4-MU). Thus K1 and 4-MU were polymerized to obtain 4-methyl-2-oxo-2H-1-benzopyran-7-yl 4,5,7,8,9-penta-O-acetyl KDN (K2).

K2 (0.5 g) was added with 4 ml of methanol and then with 4 ml of 0.5N sodium hydroxide, and it was suspended therein, followed by being left to stand at 37° C. for 1 hour. Further, 4 ml of sodium hydroxide was added thereto, followed by being left to stand at 37° C. for 90 minutes. After that, pH was neutralized by adding Dowex 50 ($H^+$) resin to give pH 6.0. The resin was removed by filtration, and the solvent was removed. A small amount of aqueous ammonia (10 mM) was added to the residue to give pH 9, followed by being subjected to Sephadex G-25 gel filtration to purify 4-MU-KDN in high purity.

Alternatively, 4-MU-KDN may be also obtained in accordance with a method described by Schreiner, E. and Zbiral, E. (1990) *Liebigs Ann. Chem.*, 581–586.

(2) Cetylpyridinium chloride (CPC) method

KDN-containing glycoprotein originating from ovarian liquid of rainbow trout was used as a substrate. The enzyme reaction was performed under the same condition as described in the foregoing item (1). After that, 2 ml of 0.1% cetylpyridinium chloride (CPC.) was added to the reaction solution. The KDN-containing glycoprotein formed a complex in the presence of CPC and precipitated. However, KDN liberated by the enzyme reaction did not precipitate. The reaction solution was left to stand for 30 minutes, followed by centrifugation (3,000 rpm, 10 minutes) to obtain a supernatant. The enzyme activity was measured by quantitatively measuring the amount of KDN in the obtained supernatant in accordance with a thiobarbituric acid method (*Analytical Biochemistry*, Vol. 205, pp. 244–250 (1992)). An amount of the enzyme, which hydrolyzed 1 nmol of KDN-containing glycoprotein per 1 minute at 25° C., was defined as 1 unit.

EXAMPLE 1

Acquisition of Sphingobacterium mOL12-4s

Sludge obtained in a fish farm was inoculated into M9 liquid medium (containing 6.0 g of $Na_2HPO_4$, 3.0 g of $KH_2PO_4$, 1.0 g of $NH_4Cl$, 0.5 g of NaCl, 1 mM $MgSO_4$, and 0.1 mM $CaCl_2$ in a volume of 1 L) added with 0.05% KDN oligosaccharide alcohol (prepared in accordance with a method described in *J. Biol. Chem.*, 265, 21811–21819 (1990)) to perform cultivation at 25° C. for 48 hours. An obtained culture liquid was streaked on an M9 agar medium plate containing KDN oligosaccharide alcohol to perform cultivation at 25° C. for 48 hours. Thus 66 colonies were obtained as microorganisms which grew based on the use of KDN oligosaccharide alcohol as a sole carbon source.

The microorganisms corresponding to the formation of the colonies respectively were inoculated into M9 liquid medium containing 0.05% KDN oligosaccharide alcohol to perform cultivation, and microbial cells were collected by means of centrifugation. The obtained microbial cells were disrupted by means of an ultrasonic treatment. The KDNase activity and the sialidase activity in cell-disrupted solutions were measured in accordance with the 4-MU-KDN method. Among them, a cell-disrupted solution, in which the KDNase activity was found and the sialidase activity was not found, originated from a microorganism which was designated as mOL12 and used for the following selection.

The colony of the mOL12 strain was streaked on M9 agar medium containing 0.05% KDN oligosaccharide alcohol. Colonies of four strains were separated therefrom, and they were designated as mOL12-1, mOL12-2, mOL12-3, and mOL12-4 respectively. The respective colonies were streaked on LB plate medium to obtain single colonies which were inoculated into M9 liquid medium containing 0.05% KDN oligosaccharide alcohol to perform cultivation. Cell-disrupted solutions were prepared therefrom, for which the KDNase activity and the sialidase activity were measured respectively in accordance with the 4-MU-KDN method and the cetylpyridinium chloride method. Colonies, which were formed by streaking mOL12-4 on LB plate medium, were classified into three types in size, i.e., "large", "middle", and "small". Among them, the KDNase activity was not found in strains which formed "large" colonies and "middle" colonies. However, strains, which formed "small" colonies, exhibited the KDNase activity and did not exhibit the sialidase activity. A strain was selected from the strains which exhibited only the KDNase activity, and this strain was designated as mOL12-4s.

The mOL12-4s strain isolated as described above was identified by using a commercially available kit for identifying Gram-negative rods other than enterobacteria (produced by Biomeleu, API 20NE). Principal microbiological features tested are as follows:

| form | rod |
|---|---|
| Gram stain | negative |
| spore formation | − |
| motility | − |
| attitude to oxygen | aerobic |
| indole production | − |
| glucose fermentation | − |
| urea degradation | + |
| esculin degradation | + |
| assimilation | |
| glucose | + |
| L-arabinose | + |
| D-mannose | + |
| D-mannitol | − |
| maltose | + |
| catalase | + |
| oxidase | + |
| β-galactosidase | + |

According to the result described above, the mOL12-4s strain was identified to be a bacterium belonging to the genus Sphingobacterium, and it was designated as Sphingobacterium mOL12-4s. This microorganism has been deposited on May 24, 1994 in National Institute of Bioscience and Human Technology of Agency of Industrial Science and Technology of Ministry of International Trade and Industry under a deposition number of FERM P-14325, transferred to international deposition based on the Budapest Treaty on May 26, 1995, and deposited under a deposition number of FERM BP-5116. According to the microbiological features, this microorganism is highly possibly *Sphingobacterium multivorum*.

EXAMPLE 2

Production of KDNase

Culture liquid composed of Miller's Luria Broth (LB, produced by Gibco BRL) in an amount of 800 ml was dispensed and poured into 2 liter Erlenmeyer flask, and autoclaved. Sphingobacterium mOL12-4s was inoculated into this medium, and cultivated at 25° C. for 48 hours by using a shaker.

<1> Extraction of KDNase and Ammonium Sulfate fractionation (1) Extraction of KDNase by microbial cell disruption and ammonium sulfate fractionation After completion of the cultivation, microbial cells were collected from the culture liquid by means of centrifugation (15,000× g, 40 minutes). The obtained microbial cells were suspended in ice-cooled 0.1M Tris-HCl buffer (pH 8.0) containing 0.1M NaCl, and the microbial cells were washed by performing centrifugation again. This washing operation was repeated three times. After that, the microbial cells were suspended in 0.1M NaCl-20 mM Tris-HCl buffer (pH 8.0) in a volume of ½ of that of the microbial cells. The microbial cells were disrupted by means of an ultrasonic treatment (50 watts, 5 minutes).

The cell-disrupted solution was centrifuged (17,000× g, 40 minutes) to obtain a supernatant which was cooled. Ammonium sulfate was added to the supernatant to achieve 50% saturation, followed by being left to stand at 4° C. for 1 hour. The solution was centrifuged at 150,000× g for 1 hour to remove a precipitate. An obtained supernatant was added with ammonium sulfate to achieve 70% saturation, followed by being left to stand at 4° C. overnight. The solution was centrifuged again at 150,000× g for 1 hour to obtain a precipitate which was dissolved in 10 ml of 0.5M NaCl-20 mM Tris-HCl buffer (pH 8.0). A saturated ammonium sulfate aqueous solution was added to the obtained solution to achieve 43% saturation, followed by being left to stand at 4° C. for 1 hour. The solution was centrifuged at 150,000× g for 1 hour to obtain a supernatant which was added with ammonium sulfate to achieve 85% saturation, followed by being left to stand at 4° C. overnight. A produced precipitate was recovered by means of centrifugation at 150,000× g for 1 hour, and the recovered precipitate was dissolved in 10.9 ml of 0.5M NaCl-20 mM Tris-HCl buffer (pH 8.0). The fraction thus obtained was designated as 50–70% ammonium sulfate precipitation fraction.

(2) Extraction of KDNase by osmotic shock and ammonium sulfate fractionation

Another method for extracting KDNase from microbial cells was used to release the enzyme to the outside of the microbial cells by applying osmotic shock to the microbial cells. An obtained extracellular solution was subjected to ammonium sulfate fractionation to purify KDNase.

Sphingobacterium mOL12-4s was cultivated in the same manner as described above. Microbial cells were collected and washed by means of centrifugation (15,000× g, 40 minutes). The microbial cells were subjected to an osmotic shock treatment in accordance with a known method [Nossal, N. G. and Heppel, L. A. (1966) *J. Biol. Chem.*, 241, 3055–3062] to release the enzyme to the outside of the microbial cells. Namely, the microbial cells were suspended in 20 mM Tris-HCl buffer (pH 7.1) containing 20% sucrose in an amount of 40 ml with respect to 1 g of the microbial cells, followed by being left to stand for 10 minutes. After that, the microbial cells were precipitated by means of centrifugation operation (13,000× g, 30 minutes). Osmotic shock was given to the microbial cells by suspending the microbial cells in 20 mM Tris-HCl buffer (pH 7.1) containing 1 mM magnesium chloride, and being left to stand for 10 minutes.

The suspension of the microbial cells was centrifuged again (13,000× g, 30 minutes) to remove the microbial cells. An obtained supernatant was immediately added with ammonium sulfate to achieve 90% saturation, followed by being left to stand at 4° C. overnight. A produced precipitate was collected by centrifugation (15,000× g, 30 minutes), and suspended and dissolved in a 50% saturated ammonium sulfate solution, from which insoluble suspending matters were removed by means of centrifugation (15,000× g, 30 minutes). Ammonium sulfate was added to an obtained supernatant to achieve 70% saturation, followed by being left to stand at 4° C. overnight. The solution was centrifuged again (15,000× g, 30 minutes) to obtain a precipitate fraction which was collected as a 50–70% ammonium sulfate precipitation fraction.

(3) Induction of KDNase in Sphingobacterium mOL12-4s (3-1) Preparation of inducer KDN and KDN oligosaccharide alcohol (represented by KDNα2→3Galβ1→3GalNAcα1→3 [KDNα2→(8KDNα2→)$_n$→6 ]GalNacol, wherein n=5, hereinafter referred to as "KDN-OS", if necessary) were prepared in accordance with a known method (Kitajima, K. et al., *J. Biol. Chem.*, 269, 21415–21419 (1994)). A fraction rich in KDN-OS (hereinafter referred to as "crude KDN-OS", if necessary) was prepared as follows. Ovarian liquid of rainbow trout (12.3 L) was concentrated and lyophilized to obtain 110 g of dry powder. The lyophilized powder (50 g) was subjected to extraction once with 1.0 L of chloroform/methanol (2:1, v/v), and subjected to extraction with 1.0 L of chloroform/methanol (1:2, v/v) at room temperature for 2 hours (see Yu, S. et al., *Biochemistry*, 32, 9221–9229 (1993)). The degreased residue was dried in air to measure its weight which was 39 g. The degreased ovarian liquid powder (10 g) was suspended in 100 ml of 1M NaBH$_4$/0.1M NaOH, and incubated with agitation at 37° C. After incubation for 24 hours, 50 ml of the same solution (1M NaBH$_4$/0.1M NaOH) was added thereto, followed by further incubation for 24 hours. The reaction mixture was centrifuged at 9,000× g for 20 minutes, followed by neutralization with glacial acetic acid to achieve pH of about 6. After that, a supernatant was desalinized by using Sephadex G-25 (produced by Pharmacia) chromatography (2.0×150 cm, eluted with water). The desalinated fraction abundantly contained KDN-OS, which was designated as crude KDN-OS. KDN was quantitatively measured in accordance with a TBA method (Kitajima, K. et al., *Anal. Biochem.*, 205, 244–250 (1992)).

(3-2) Experiment for inducing enzyme

Bacterial cells (4.0×10$^8$) of Sphingobacterium mOL12-4s were inoculated into 40 ml of M9 liquid medium containing 1% (w/v) casein hydrolysate (casamino acid, produced by Gibco) and 1% (w/v) glucose (Glc), and cultivated at 25° C. for 44 hours. Microbial cells (bacterial cells) at the growth phase were collected, and washed twice with M9 liquid medium. The microbial cells (6.1×10$^{10}$ cells) were inoculated into 2.0 ml of M9 liquid medium containing 0.1% (w/v) crude KDN-OS, KDN-OS, KDN, Neu5Ac, acid hydrolysate of colominic acid (oligo-Neu5Ac; Kitazume, S. et al., *Anal. Biochem.*, 202, 25–34 (1992)), or Glc, and incubated at 25° C. for 24 hours to measure the number of growable cells and the KDNase activity. The number of cells was determined by diluting each incubated cell cultivation liquid to inoculate an obtained diluted solution into an LB agar medium plate, and counting a number of grown colonies (Kitajima, K. et al., *J. Biol. Chem.*, 269, 21415–21419). In order to measure the KDNase activity of the cells, the cells were collected by means of centrifugation at 5,000 rpm or 1,500× g for 10 minutes. The collected cells were suspended in 0.5 ml of 100 mM Tris-acetate buffer (pH 6.0) containing 100 mM NaCl, and disrupted by means of ultrasonication (50 watts, 1 minute). The disrupted preparation was centrifuged at 10,000 rpm or 6,000× g for 10 minutes to subsequently obtain a supernatant for which the KDNase activity was measured. Results are shown in Table 1. The numerical value in [] in Table 1 indicates a ratio provided that the activity before the addition is regarded as 1.

TABLE 1

| Added substance | Number of cells | KDNase activity (milliunit) | KDNase activity per cells (milliunit/10$^{10}$ cells) |
|---|---|---|---|
| Before addition | 6.1 × 10$^{10}$ [1] | 20 [1] | 3.3 [1] |
| Glc | 1.7 × 10$^{12}$ [28] | 80 [4] | 0.47 [0.14] |
| KDN-OS | 1.5 × 10$^{12}$ [25] | 7500 [380] | 50 [15] |
| crude KDN-OS | 5.7 × 10$^{12}$ [93] | 23000 [1200] | 40 [12] |
| KDN | 3.6 × 10$^{10}$ [0.59] | 38 [1.9] | 11 [3.3] |
| Neu5Ac | 2.5 × 10$^{10}$ [0.41] | 15 [0.75] | 6.0 [1.8] |
| Oligo-Neu5Ac | 3.0 × 10$^{10}$ [0.49] | 12 [0.60] | 4.0 [1.2] |

The KDNase activity per a number (10$^{10}$) of cells, which was obtained when 0.1% crude KDN-OS was added, was measured along with passage of time. A result is shown in FIG. 1.

As a result, KDN, KDN-OS, and crude KDN-OS induced KDNase, however, the other monosaccharides and oligosaccharide had no effect on induction of the enzyme. Free KDN also induced KDNase, however, an effect equivalent to those obtained with KDN-OS and crude KDN-OS was not observed. According to this fact, it was suggested that a substance having the ketosidic linkage formed by KDN was preferred as an inducer.

According to FIG. 1, it was demonstrated that when proliferating cells (6.0×10$^{10}$) were cultivated in M9 medium containing 0.1% KDN-OS, the KDNase activity per cell is increased to a level extremely higher than that of an initial activity after incubation for 24 hours to 43 hours.

<2> Purification of KDNase

Figure 2:
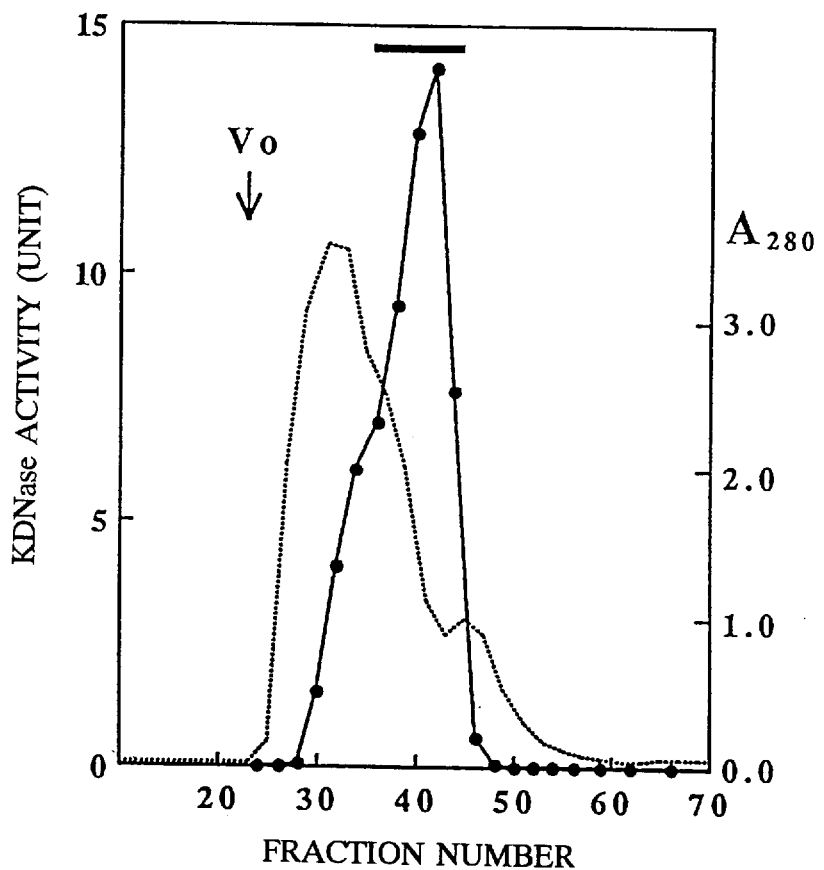
FIG. 2 shows an elution pattern of first Sephacryl S-200 gel filtration chromatography used during purification of the enzyme of the present invention. A solid line represents the enzyme activity, and a broken line represents ultraviolet absorption (A280) indicating the amount of protein.
Figure 3:
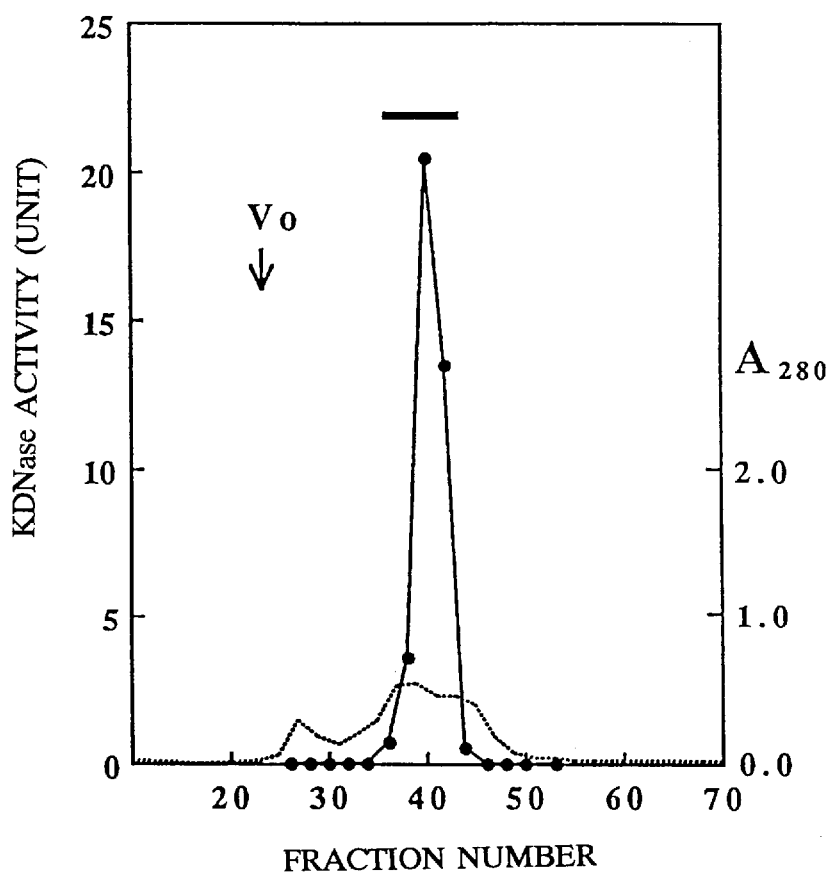
FIG. 3 shows an elution pattern of second Sephacryl S-200 gel filtration chromatography used during purification of the enzyme of the present invention. A solid line represents the enzyme activity, and a broken line represents ultraviolet absorption (A280) indicating the amount of protein.

The total amount of the 50–70% ammonium sulfate precipitation fraction obtained as described in the foregoing item (1) was applied to a Sephacryl S-200 (produced by Pharmacia) column (1.8×135 cm), which was eluted with 20 mM Tris-HCl buffer (pH 8.0) containing 0.5M NaCl. Thus fractionation by gel filtration was performed (FIG. 2). The KDNase activity was measured for each of eluted fractions in accordance with the 4-MU-KDN method. Active fractions were collected, to which ammonium sulfate was added to achieve 90% saturation, followed by being left to stand overnight. The solution was centrifuged at 150,000× g for 1 hour to obtain a precipitate which was dissolved in 4.7 ml of 20 mM Tris-HCl buffer (pH 8.0)/0.5M NaCl. Gel filtration was performed again in the same manner as described above by using a Sephacryl S-200 column to collect KDNase active fractions (FIG. 3).

Figure 4:
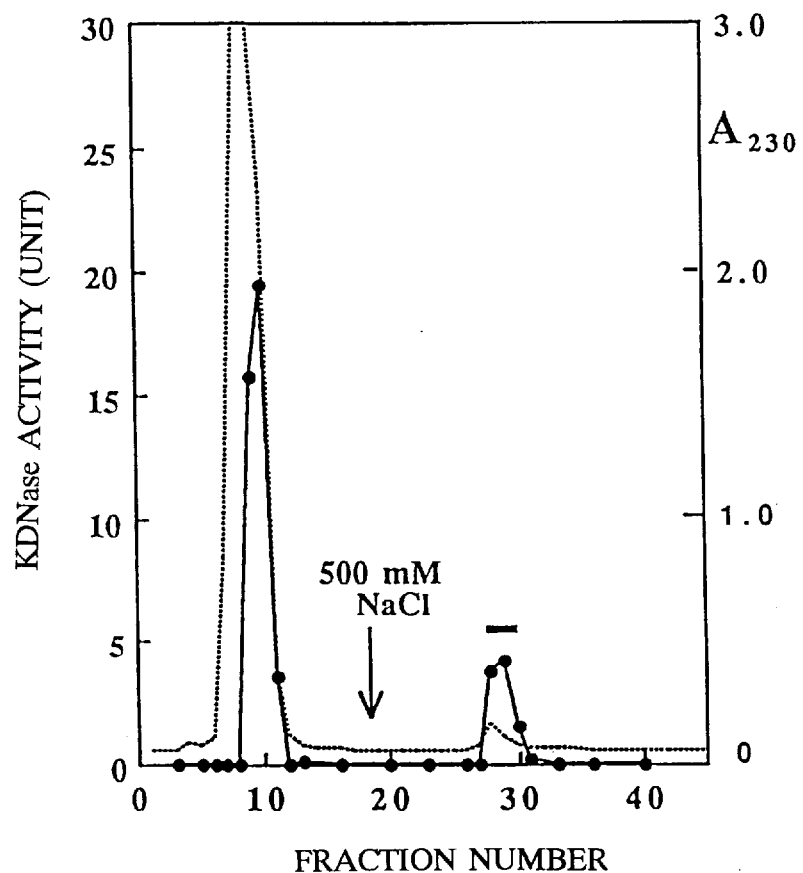
FIG. 4 shows an elution pattern of first affinity chromatography with KDN-gp-linked agarose gel used during purification of the enzyme of the present invention. A solid line represents the enzyme activity, and a broken line represents ultraviolet absorption (A230) indicating the amount of protein.
Figure 5:
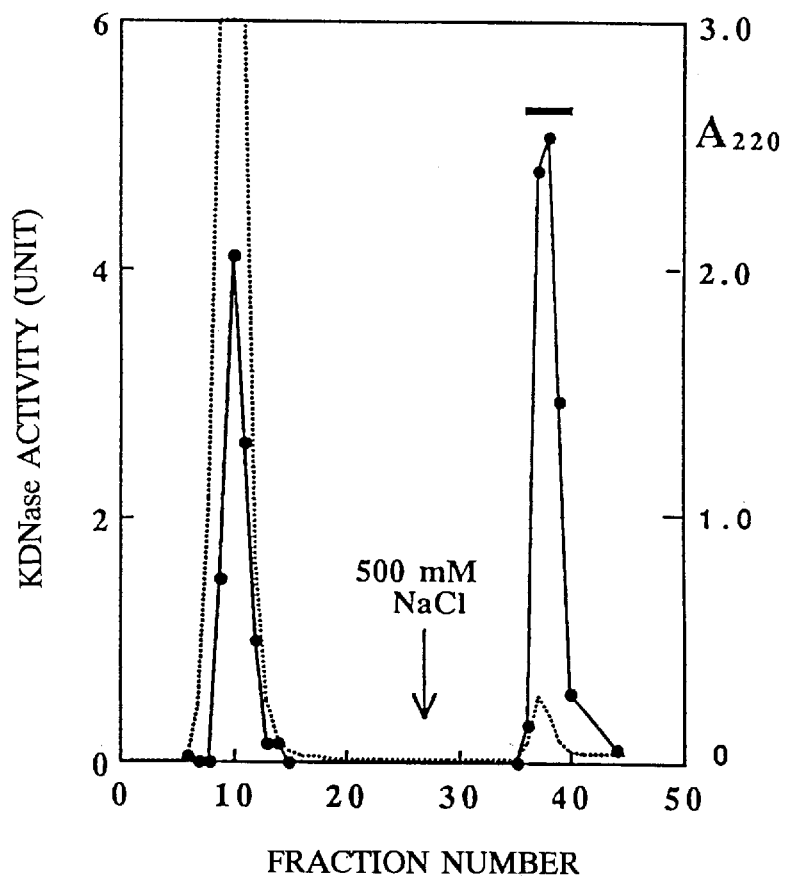
FIG. 5 shows an elution pattern of second affinity chromatography with KDN-gp-linked agarose gel used during purification of the enzyme of the present invention. A solid line represents the enzyme activity, and a broken line represents ultraviolet absorption (A220) indicating the amount of protein.
Figure 6:
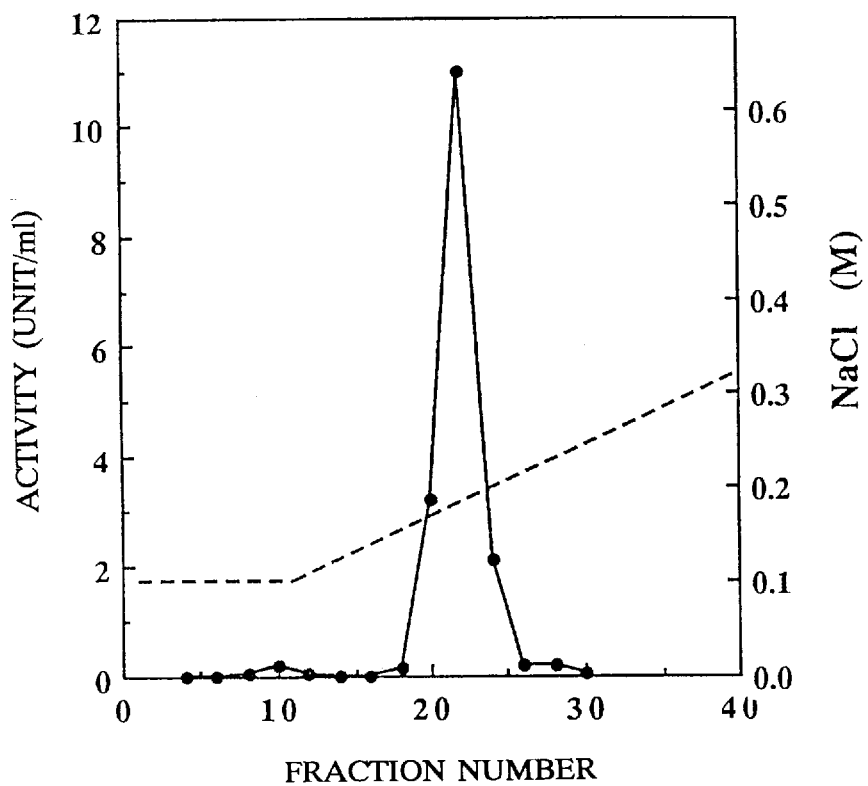
FIG. 6 shows an elution pattern of second CM-Toyopearl 650M column chromatography used during purification of the enzyme of the present invention (single purified enzyme). A solid line represents the enzyme activity, and a broken line represents the concentration of NaCl used for elution.

The KDNase active fractions were collected, to which ammonium sulfate was added to achieve 90% saturation, followed by being left to stand overnight. The solution was centrifuged at 150,000× g for 1 hour to obtain a precipitate which was dissolved in 4.8 ml of 20 mM Tris-acetate buffer (pH 6.0)/0.05M NaCl. This solution was applied to a column (2.0×15 cm) charged with agarose gel (Affi-gel 15, produced by Bio Rad) with KDN-containing glycoprotein (KDN-gp) linked thereto, which was eluted by successively using 90 ml of 20 mM Tris-acetate buffer (pH 6.0)/0.05M NaCl and 135 ml of 20 mM Tris-acetate buffer (pH 6.0)/0.5M NaCl (FIG. 4). A part of the active fraction was not adsorbed because of overcharge exceeding the adsorbing capacity of the column. The non-adsorbed part of the active fraction was applied and adsorbed to the aforementioned column again as it is, which was then eluted with 20 mM Tris-acetate buffer (pH 6.0)/0.5M NaCl (FIG. 5). Thus all enzyme fractions, which were adsorbed to the agarose gel with KDN-gp linked thereto, and then eluted by high ionic strength, were collected (15 ml). The collected enzyme fraction was concentrated up to 2 ml by means of ultrafiltration (Centriflow CF25, produced by Amicon), which was designated as an affinity-purified enzyme fraction.

The enzyme activity, the amount of protein, the yield, and the degree of purification of the obtained enzyme fractions were measured for each of purification steps. The KDNase activity was measured in accordance with the 4-MU-KDN method, wherein an amount of the enzyme to produce 1 nmol of 4-MU per 1 minute at 25° C. was defined to be 1 unit. The amount of protein was quantitatively measured in accordance with a modified Lowry method (BCA reagent; Pierce, U.S.A.), wherein absorbance at 230 nm was measured by using bovine serum albumin (BSA) as a standard. Results are shown in Table 2.

TABLE 2

| Fraction | Activity (unit) | Protein (mg) | Specific activity (unit/mg) | Yield (%) | Purification degree (fold) |
| --- | --- | --- | --- | --- | --- |
| cell-disrupted solution | 153 | 207 | 0.737 | 100 | 1.0 |
| 50–70% $(NH_4)_2SO_4$ fraction | 113 | 103 | 1.11 | 74.2 | 1.5 |
| 1st Sephacryl S-200 | 76.1 | 57.3 | 1.33 | 49.8 | 1.8 |
| 2nd Sephacryl S-200 | 57.4 | 26.6 | 2.16 | 37.6 | 2.9 |
| KDN-gp agarose adsorbed fraction | 52.2 | 0.410 | 127 | 34.2 | 173 |

Figure 7:
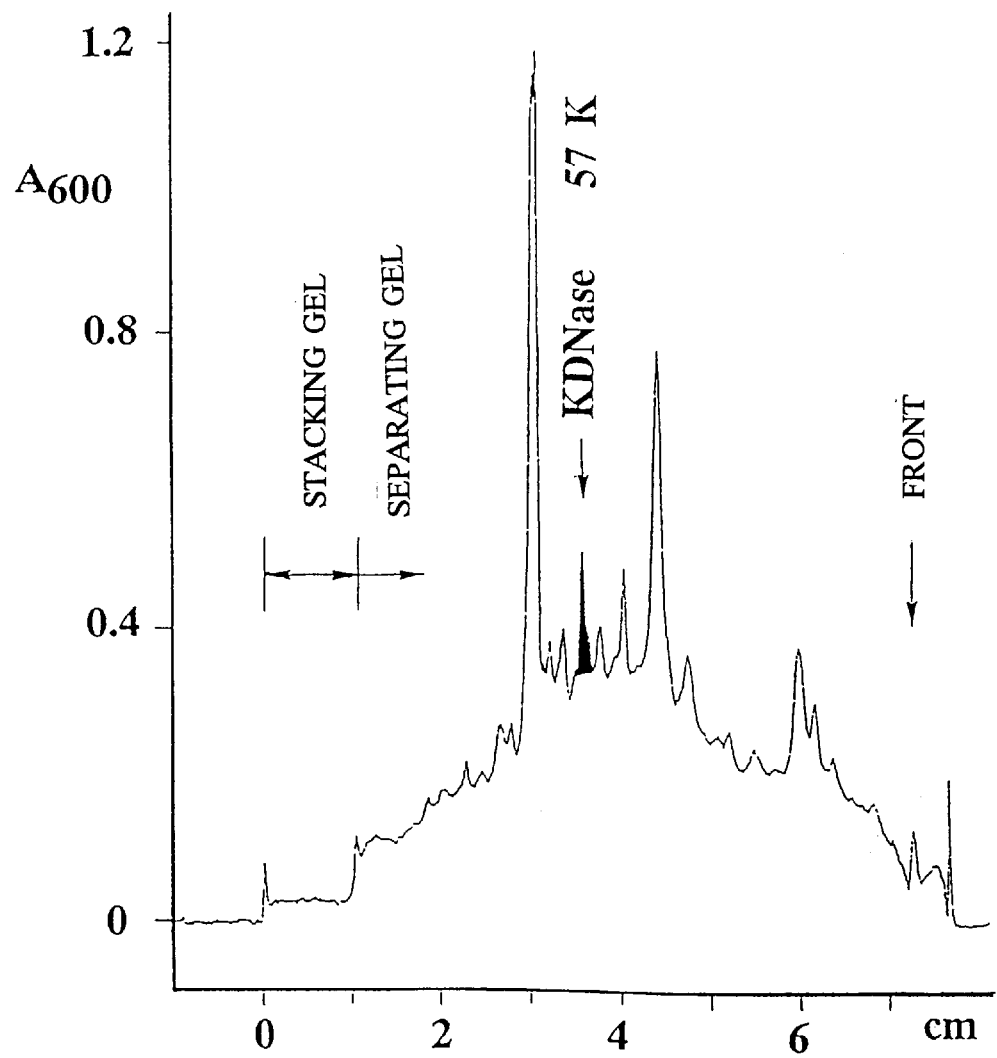
FIG. 7 shows a result of 10% acrylamide gel electrophoresis for an affinity-purified enzyme fraction. Positions and staining strengths of respective bands after silver staining were analyzed by using a densitometer (to measure absorbance at 600 nm).

The affinity-purified enzyme fraction was subjected to 10% SDS-polyacrylamide gel electrophoresis (SDS-PAGE). After the electrophoresis, the gel was stained with a silver staining kit (produced by Wako Pure Chemical). Positions and densities of stained five or six bands were measured by using a densitometer (to measure absorbance at 600 nm). A result is shown in FIG. 7.

The enzyme fraction was further fractionated by using a Sephacryl S-200 gel filtration column to obtain seven fractions having the KDNase activity eluted at Kav 0.3 to 0.4. The relationship between the KDNase activity and the behavior of bands detected by SDS-polyacrylamide gel electrophoresis was investigated in detail for the seven fractions. As a result, a band corresponding to one component was found, in which the appearing pattern of the band was coincident with the magnitude of the activity, which was estimated to be the band of KDNase. This band had an apparent molecular weight calculated to be 57,000 on the basis of comparison with molecular weight markers (produced by Seikagaku Corporation). On the other hand, the molecular weight of the active component, estimated from the gel filtration chromatography, was calculated to be 50,000 on the basis of comparison with molecular weight markers (produced by Seikagaku Corporation), which was approximately coincident with the result obtained by SDS-PAGE. FIG. 7 shows a pattern of SDS-PAGE of the affinity-purified enzyme fraction, and a position of the band considered to be KDNase.

KDNase was not completely purified by the foregoing purification steps. However, both of the crude enzyme solutions such as the cell-disrupted solution, and the affinity-purified enzyme fraction can be used as KDNase having no sialidase activity. The enzyme may be further purified in accordance with ordinary enzyme purification methods, if necessary. In such a procedure, the KDNase activity and the estimated molecular weight may be used as indexes.

The present inventors succeeded in purifying KDNase up to a homogeneous level on SDS-PAGE by using, for example, the following method. A supernatant of a cell-disrupted solution, which was obtained by an osmotic shock treatment for microbial cells, was added with solid ammonium sulfate little by little up to 90% saturation while performing mild agitation, followed by being left to stand at 4° C. overnight. A precipitate was recovered by means of centrifugation at 17,000× g for 30 minutes. The recovered precipitate was dissolved in 10 ml of 0.1M NaCl-100 mM Tris-acetate buffer (pH 6.0), and dialyzed against 0.1M NaCl-0.25M sucrose-20 mM Tris-acetate buffer (pH 6.0). The solution was applied to a CM-Toyopearl 650M column (2.2×11 cm, 42 ml; produced by Toyo Soda) equilibrated with the same dialysis buffer (0.1M NaCl-0.25M sucrose-20 mM Tris-acetate buffer (pH 6.0)), which was firstly eluted with 60 ml of the same buffer (0.1M NaCl-0.25M sucrose-20 mM Tris-acetate buffer (pH 6.0)), and then eluted with 400 ml of linear concentration gradient of NaCl (from 0.1M to 0.6M) in 0.25M sucrose-20 mM Tris-acetate buffer (pH 6.0). Pass-through fractions were combined into a solution which was concentrated to 15 ml by means of ultrafiltration (YM10, produced by Amicon). The concentrated solution was applied to a DEAE-Toyopearl 650M column (2.2×11 cm, 42 ml; produced by Toyo Soda) equilibrated with 0.1M NaCl-0.25M sucrose-20 mM Tris-HCl buffer (pH 8.0), which was firstly eluted with 60 ml of the same buffer as that used for the equilibration (0.1M NaCl-0.25M sucrose-20 mM Tris-HCl buffer (pH 8.0)), and then eluted with 60 ml of 0.5M NaCl-0.25M sucrose-20 mM Tris-HCl buffer (pH 8.0). Fractions not adsorbed to the column were pooled to obtain a pooled solution which was concentrated to 13 ml by means of ultrafiltration. The concentrated solution was applied to a CM-Toyopearl 650M column equilibrated with 0.1M NaCl-0.25M sucrose-20 mM Tris-HCl buffer (pH 8.0), which was firstly eluted with 0.1M NaCl-0.25M sucrose-20 mM Tris-HCl buffer (pH 8.0), and then eluted with linear concentration gradient of NaCl (from 0.1M to 0.6M) in 0.25M sucrose-20 mM Tris-HCl buffer (pH 8.0) to collect fractions having the KDNase activity (in the vicinity of 0.17 to 0.2M of NaCl). The fractions were combined into a solution which was subjected to SDS-PAGE. As a result, a single band was confirmed.

The single purified enzyme thus obtained had an apparent molecular weight calculated to be about 42,000 on the basis of comparison with molecular weight markers on SDS-PAGE. A molecular weight was estimated from gel filtration chromatography (Sephacryl S-200 column, 1.8 cm×135 cm; eluted with 20 mM Tris-HCl buffer (pH 8.0)/0.2M NaCl), which was calculated to be about 40,000 on the basis of comparison with molecular weight markers.

<3> Properties of the Enzyme of the Present Invention

Properties of the enzyme of the present invention were investigated by using the affinity-purified enzyme fraction obtained as described above.

(1) Substrate specificity

The reactivity of the enzyme of the present invention was investigated for various KDN-containing complex carbohydrates and carbohydrates and sialic acid-containing complex carbohydrates and carbohydrates.

Methods or sources for obtaining KDN-containing complex carbohydrates and carbohydrates and sialic acid-containing complex carbohydrates and carbohydrates used herein are as follows.

KDN dimer, N-acetylneuraminic acid (Neu5Ac) dimer, N-glycolylneuraminic acid (Neu5Gc) dimer: *Anal. Biochem.*, 202 25–34 (1992).

KDN-containing double strand N-type sugar chain: *Biochemistry,* 33, 6495–6502 (1994).

KDN oligosaccharide alcohol, KDN-containing glycoprotein: *J. Biol. Chem.,* 265, 21811–21819 (1990).

KDN-containing ganglioside GM3: *J. Biol. Chem.,* 266, 21929–21935 (1991).

4-Methylumbelliferyl Neu5Ac, colominic acid: purchased from Nakarai Chemical.

N-Acetylneuraminic acid lactose, human transferrin, fetal bovine serum fetuin: purchased from Sigma.

Neu5Ac-containing double strand N-type sugar chain: *J. Biol. Chem.,* 264, 18520–18526 (1989).

Swine submandibular gland mucin: *Arch. Biochem. Biophys.,* 129, 49–56 (1969).

Lake trout polysialoglycoprotein, rainbow trout polysialoglycoprotein, arctic char polysialoglycoprotein: *J. Biol. Chem.,* 268, 23675–23684 (1993).

Neu5Ac-containing ganglioside GM3, Neu5Ac-containing ganglioside GM1: *Biochem. J.,* 441, 488–497 (1976).

Neu5Acα2→6(Galβ1→3)GalNAcol, toad ovum jelly glycoprotein: *Eur. J. Biochem.,* 223, 223–231 (1994).

Each of the foregoing complex carbohydrates or carbohydrates containing KDN or sialic acid, which corresponded to 5 μg of KDN or N-acetylneuraminic acid (Neu5Ac) or N-glycolylneuraminic acid (Neu5Gc), was allowed to coexist with the enzyme of the present invention (80 milliunits) at 25° C. for 20 hours in 10 μl of 0.1M Tris-acetate buffer (pH 6.0) containing 0.1M NaCl.

The reaction solution was spotted on a plate for silica gel thin layer chromatography (produced by Merck), and developed for 7 hours with 1-propanol: 25% aqueous ammonia: water=6:1:2.5 (volume ratio). After the development, the plate was dried, on which 10% sulfuric acid ethanol solution was sprayed. The plate was heated at 120° C. to cause color development for the complex carbohydrates or carbohydrates and liberated KDN, Neu5Ac, or Neu5Gc. A control was provided, in which the reaction was performed without addition of the enzyme. Results are shown in Table 3. Those in which KDN, Neu5Ac, or Neu5Gc was liberated are indicated by "+", and those in which KDN, Neu5Ac, or Neu5Gc was not liberated at all are indicated by "–".

TABLE 3

| Complex carbohydrate or carbohydrate | Linkage | Presence or absence of cleavage |
|---|---|---|
| 4-MU-KDN | | + |
| KDN dimer | KDNα2→8KD | + |
| KDN-containing double strand N-type sugar chain | KDNα2→3Gal | + |
| KDN oligosaccharide alcohol | KDNα2→8KDN, KDNα2→3Gal KDNα2→6GalNAcol | + |
| KDN-containing glycoprotein | KDNα2→8KDN, KDNα2→3Gal KDNα2→6GalNAc | + |
| KDN-containing ganglioside GM3 | KDNα2→3Gal | + |
| 4-MU-Neu5Ac | | – |
| Neu5Ac dimer | Neu5Acα2→8Neu5Ac | – |
| Neu5Gc dimer | Neu5Gcα2→8Neu5Gc | – |
| Neu5Ac lactose | Neu5Acα2→3(6)Gal | – |
| Neu5Ac-containing double strand N-type sugar chain | Neu5Acα2→3Gal | – |
| Neu5Acα2→6(Galβ1→3)GalNAcol | Neu5Acα2→6GalNAcol | – |
| human transferrin | Neu5Acα2→6Gal | – |
| fetal bovine serum fetuin | Neu5Acα2→3(6)Gal | – |
| swine submandibular gland mucin | Neu5Gcα2→6GalNAc | – |
| toad ovum jelly glycoprotein | Neu5Acα2→6GalNAc | – |
| colominic acid | (→8Neu5Acα2→)$_n$ | – |
| lake trout polysialoglycoprotein | (→8Neu5Acα2→)$_n$ | – |
| rainbow trout polysialoglycoprotein | (→8Neu5Gcα2→)$_n$ | – |
| arctic char polysialoglycoprotein | (→8Neu5Acα2→, →8Neu5Gcα2→)$_n$ | – |
| Neu5Ac-containing ganglioside GM3 | Neu5Acα2→3Gal | – |
| Neu5Ac-containing ganglioside GM1 | Neu5Acα2→3(GalNAcβ1→4)Gal | – |

According to the result, it has been clarified that the enzyme of the present invention acts on not only 4-MU-KDN as a synthetic substrate but also any of ketosidic linkages of naturally existing known linkage forms α2→3, α2→6, and α2→8 formed by the KDN residue.

As for the various complex carbohydrates and carbohydrates containing N-acetylneuraminic acid and N-glycolylneuraminic acid shown in Table 3, the enzyme of the present invention did not hydrolyze the ketosidic linkage formed by N-acetylneuraminic acid or N-glycolylneuraminic acid. Accordingly, the enzyme of the present invention is highly specific to deaminoneuraminic acid.

(2) Optimum pH

Figure 8:
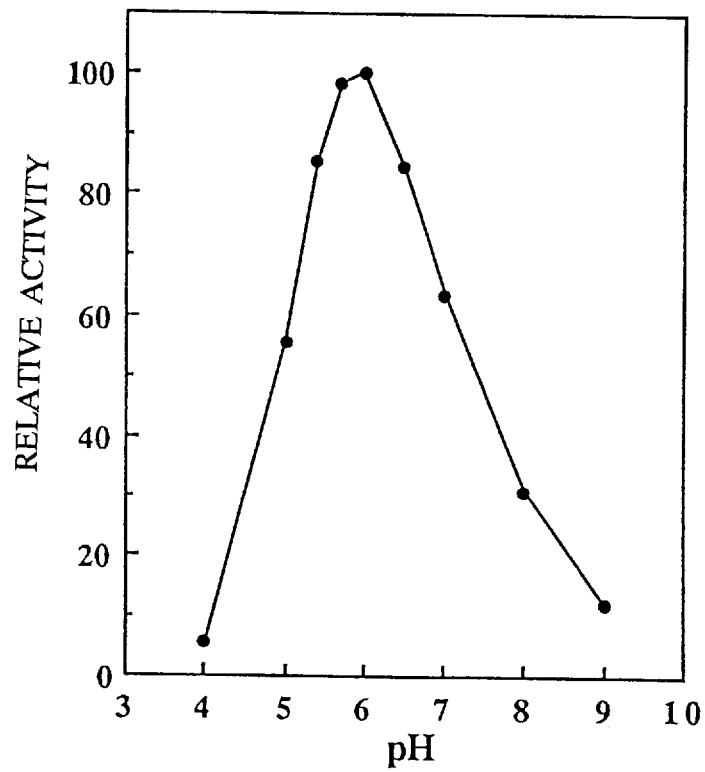
FIG. 8 shows a curve of pH-enzyme activity, illustrating optimum pH of an affinity-purified enzyme fraction of the enzyme of the present invention.
Figure 9:
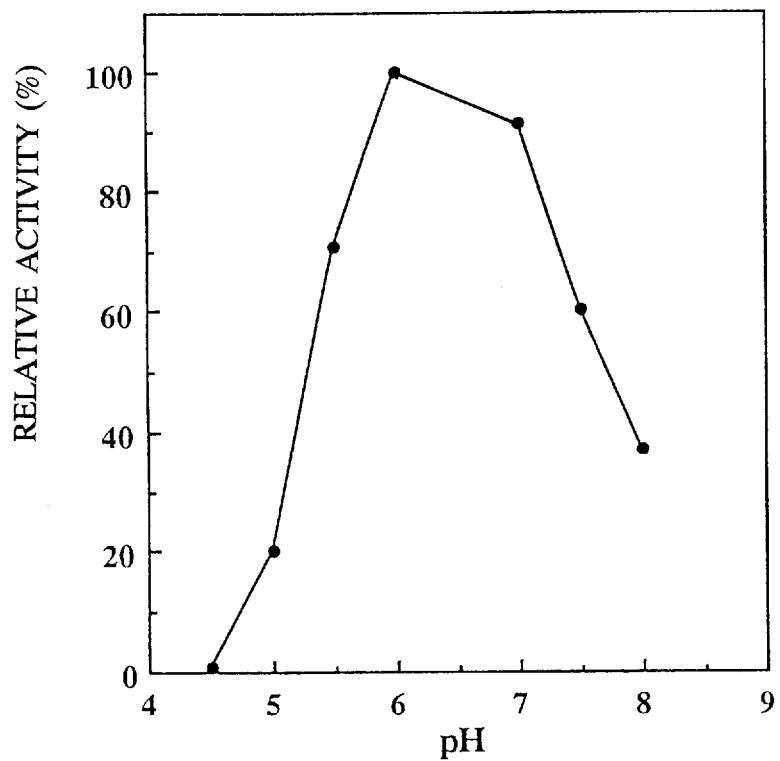
FIG. 9 shows a curve of pH-enzyme activity, illustrating optimum pH of a single purified enzyme sample of the enzyme of the present invention.

Optimum pH was measured by using the affinity-purified enzyme fraction of the enzyme of the present invention and the single purified enzyme obtained as described above. The enzyme reaction was performed in accordance with the 4-MU-KDN method described above except that 0.1M Tris-acetate buffer was used as a buffer, and the reaction was performed at each pH ranging from pH 4.0 to 9.0 to measure the enzyme activity under each pH condition. As a result, the highest activity was obtained in the vicinity of pH 6 as shown in FIG. 8 (affinity-purified enzyme fraction) and FIG. 9 (single purified enzyme).

(3) Optimum temperature

The KDNase activity was measured in accordance with the 4-MU-KDN method described above except that the temperature condition was changed. As a result, the enzyme of the present invention exhibited higher activities in the vicinity of 25° to 30° C.

(4) Stability

The enzyme of the present invention was left to stand for several hours under conditions of 25° C. and pH 4 to 9. After that, the KDNase activity was measured in accordance with the 4-MU-KDN method. The enzyme of the present invention was relatively stable in this pH range.

The enzyme of the present invention was dissolved in 0.1M Tris-acetate buffer (pH 6.0)/0.1M NaCl to give a concentration of 70 $\mu$g/ml, and it was left to stand for a predetermined period of time at various temperatures. After that, the KDNase activity was measured in accordance with the 4-MU-KDN method. As a result, the enzyme of the present invention was not inactivated at 25° C. for at least 48 hours.

The enzyme of the present invention was unstable at a concentration of several tens of $\mu$g/ml or less, regardless of pH and ionic strength. The purified enzyme was stabilized in the presence of protein such as bovine serum albumin.

(5) Inhibition and activation of the enzyme of the present invention

In order to investigate influences of, for example, inorganic ions and EDTA (ethylenediaminetetraacetic acid) on the activity of the enzyme of the present invention, these compounds were added to the reaction solution to perform the enzyme reaction in accordance with the 4-MU-KDN method. As a result, the activity was not affected by each of divalent cations, i.e., calcium ion ($Ca^{2+}$), magnesium ion ($Mg^{2+}$), and manganese ion ($Mn^{2+}$), and EDTA when they were subjected to the investigation at a concentration of 1 mM.

Figure 10:
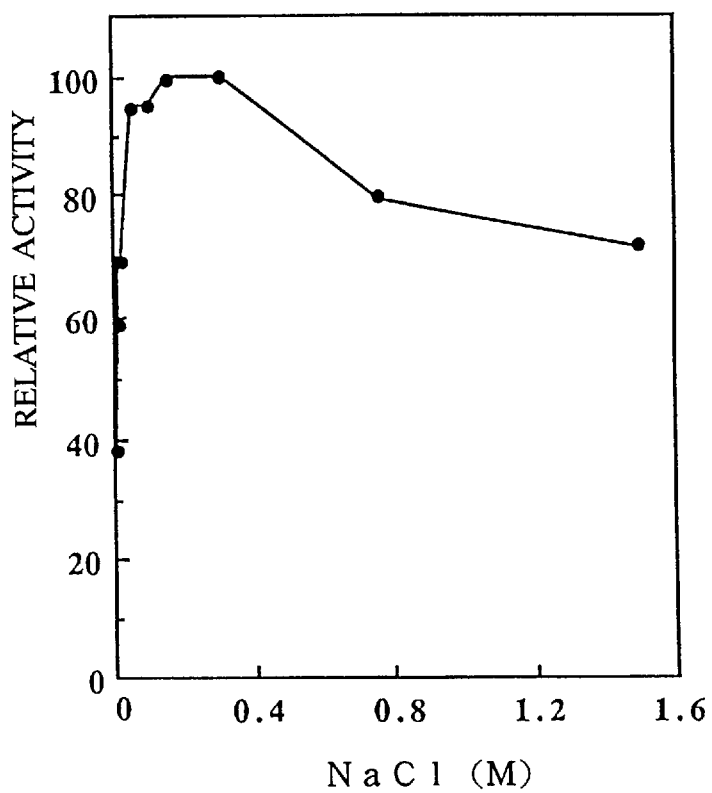
FIG. 10 shows a curve of ionic strength-enzyme activity, illustrating optimum ionic strength of the enzyme of the present invention. The ionic strength is represented by the concentration of added NaCl.

The influence of the ionic strength on the enzyme of the present invention was investigated. A result is shown in FIG. 10. The enzyme activity rapidly increased as the ionic strength increased. A maximum value was obtained in the presence of 300 mM NaCl. The activity was extremely low at a low ionic strength of 50 mM or less.

The enzyme of the present invention was inhibited by free KDN (3 mM). On the other hand, the enzyme of the present invention was not inhibited by free sialic acid as a structural analog of KDN. The enzyme of the present invention was also not inhibited by the complex carbohydrates and carbohydrates containing N-acetylneuraminic acid or N-glycolylneuraminic acid which had been revealed not to serve as a substrate of the enzyme of the present invention. The enzyme of the present invention was not inhibited by 2,3-dehydro-2-deoxy-N-acetylneuraminic acid. 2,3-Dehydro-2-deoxy-N-acetylneuraminic acid is a specific inhibitor for known sialidase which cleaves the ketosidic linkage formed by N-acylneuraminic acid.

The enzyme of the present invention was not inhibited by Triton X-100 as a surfactant. The enzyme activity of the enzyme of the present invention substantially disappeared in the presence of 0.5% sodium cholate, however, about 90% of the enzyme activity was maintained in the presence of 0.1% sodium cholate.

(6) Measurement of Michaelis constant

The Michaelis constant (Km) and the maximum enzyme reaction velocity (Vmax) were determined on condition that 4-methylumbelliferyl KDN (4-MU-KDN) was used as a substrate for the enzyme of the present invention. The enzyme (32 milliunits) and the substrate (4-MU-KDN, 6.7 $\mu$M) were reacted at 25° C. in 216 $\mu$l of a reaction solution (0.1M Tris-acetate buffer (pH 6.0)/0.1M NaCl containing 0.1 mg/ml of bovine serum albumin). As a result, 4-methylumbelliferone (4-MU) was liberated linearly within 1 hour.

At this enzyme concentration, initial reaction velocities were measured by performing the reaction at 25° C. for 30 minutes in the same reaction solution as described above while variously changing the concentration of 4-MU-KDN in a range of 21 to 167 $\mu$M. A Lineweaver-Burk plot was obtained, and thus the Michaelis constant was calculated. As a result, Vmax was 0.19 $\mu$M/min or 7.4 mM/min/mg protein, and Km was 19 $\mu$M, concerning hydrolysis of 4-MU-KDN catalyzed by the enzyme of the present invention.

(7) Amino acid analysis

The purified KDNase (single purified enzyme) was hydrolyzed with 6N hydrochloric acid at 105° C. for 24 hours to investigate its amino acid composition. A result is shown below. Numerical values represent mole %.

| | |
|---|---|
| asparagine and aspartic acid | 5.3 |
| glutamine and glutamic acid | 5.5 |
| serine | 13.6 |
| glycine | 19.8 |
| histidine | 2.0 |
| arginine | 2.0 |
| threonine | 6.7 |
| alanine | 9.0 |
| proline | 3.5 |
| tyrosine | 5.6 |
| valine | 5.9 |
| methionine | 7.6 |
| isoleucine | 3.5 |
| leucine | 4.9 |
| phenylalanine | 3.2 |
| lysine | 2.0 |

EXAMPLE 3

Synthesis of KDN-containing Sugar Chain

The enzyme of the present invention (1 unit) was added to a mixed solution (50 $\mu$l) of 40 mM KDN and 40 mM lactose, followed by being left to stand at 25° C. in 0.1M Tris-acetate buffer (pH 6.0). As a result, it was confirmed that KDN-containing lactose was present in the reaction solution after 30 minutes.

Industrial Applicability

The microorganism of the present invention produces the novel KDNase. The KDNase has no reactivity on the N-acylneuraminic acid residue on which known sialidase acts. In addition, the KDNase can act on the deaminoneuraminic acid residue which is extremely difficult to be cloven by known sialidase, and the KDNase can hydrolyze the ketosidic linkage formed by the deaminoneuraminic acid residue.

It is expected that the enzyme of the present invention is utilized for reagents useful for studies such as analysis of structure and function of deaminoneuraminic acid. The enzyme of the present invention is extremely highly specific to the ketosidic linkage formed by KDN. Accordingly, it is expected that the enzyme of the present invention is applied to detection of the ketosidic linkage formed by KDN.

New deaminoneuraminic acid-containing complex carbohydrates or carbohydrates can be created by utilizing the enzyme of the present invention for performing the reverse reaction of the hydrolysis reaction. Such new deaminoneuraminic acid-containing complex carbohydrates and carbohydrates have possibility to modify functions of N-acylneuraminic acid-containing complex carbohydrates and carbohydrates as analogs thereof, or they are expected to be utilized as new physiologically active substances.

What is claimed is:

1. An isolated deaminoneuraminidase obtainable from *Sphingobacterium multivorum* and having the following enzymological properties:

(a) the deaminoneuraminidase acts on complex carbohydrate or carbohydrate containing deaminoneuraminic acid, and hydrolyzes ketosidic linkage formed by deaminoneuraminic acid to produce free deaminoneuraminic acid and complex carbohydrate or carbohydrate containing no deaminoneuraminic acid, or complex carbohydrate or carbohydrate from which deaminoneuraminic acid is partially removed; and (b) the deaminoneuraminidase acts on complex carbohydrate or carbohydrate containing deaminoneuraminic acid, but does not act on ketosidic linkage formed by N-acetylneuraminic acid or N-glycolylneuraminic acid in complex carbohydrate or carbohydrate containing N-acetylneuraminic acid or N-glycolylneuraminic acid.

2. The deaminoneuraminidase according to claim 1, which has the following physicochemical properties:

(i) the deaminoneuraminidase has an optimum reaction pH in the vicinity of pH 6;

(ii) the deaminoneuraminidase is stable in a range of pH 4 to 9 at 25° C.;

(iii) the deaminoneuraminidase has an optimum reaction temperature in the vicinity of 25° C.;

(iv) the deaminoneuraminidase is not inactivated at 25° C. for at least 48 hours; and (v) the deaminoneuraminidase is inhibited by free deaminoneuraminic acid, and the deaminoneuraminidase is stabilized in the presence of bovine serum albumin.

3. The deaminoneuraminidase according to claim 1 or 2, wherein said *Sphingobacterium multivorum* is Sphingobacterium mOL12-4s.

4. A method for producing deaminoneuraminidase, comprising the steps of cultivating a bacterium *Sphingobacterium multivorum,* and collecting, from the cultivated bacterium, a deaminoneuraminidase having the following enzymological properties:

(a) the deaminoneuraminidase acts on complex carbohydrate or carbohydrate containing deaminoneuraminic acid, and hydrolyzes ketosidic linkage formed by deaminoneuraminic acid to produce free deaminoneuraminic acid and complex carbohydrate or carbohydrate containing no deaminoneuraminic acid, or complex carbohydrate or carbohydrate from which deaminoneuraminic acid is partially removed; and (b) the deaminoneuraminidase acts on complex carbohydrate or carbohydrate containing deaminoneuraminic acid, but does not act on ketosidic linkage formed by N-acetylneuraminic acid or N-glycolylneuraminic acid in complex carbohydrate or carbohydrate containing N-acetylneuraminic acid or N-glycolylneuraminic acid.

5. A method for producing carbohydrate and/or complex carbohydrate containing deaminoneuraminic acid, comprising the steps of mixing a deaminoneuraminidase with deaminoneuraminic acid and carbohydrate and/or complex carbohydrate under conditions sufficient for the deaminoneuraminidase to catalyze the production of a carbohydrate and/or complex carbohydrate containing deaminoneuraminic acid and recovering the carbohydrate and/or complex carbohydrate containing deaminoneuraminic acid, said deaminoneuraminidase obtainable from *Sphingobacterium multivorum* and having the following enzymological properties:

(a) the deaminoneuraminidase acts on complex carbohydrate or carbohydrate containing deaminoneuraminic acid, and hydrolyzes ketosidic linkage formed by deaminoneuraminic acid to produce free deaminoneuraminic acid and complex carbohydrate or carbohydrate containing no deaminoneuraminic acid, or complex carbohydrate or carbohydrate from which deaminoneuraminic acid is partially removed; and (b) the deaminoneuraminidase acts on complex carbohydrate or carbohydrate containing deaminoneuraminic acid, but does not act on ketosidic linkage formed by N-acetylneuraminic acid or N-glycolylneuraminic acid in complex carbohydrate or carbohydrate containing N-acetylneuraminic acid or N-glycolylneuraminic acid.

* * * * *

UNITED STATES PATENT AND TRADEMARK OFFICE
CERTIFICATE OF CORRECTION

PATENT NO. : 5,834,288
DATED : November 10, 1998
INVENTOR(S) : Yasuo Inoue and Sadako Inoue It is certified that error appears in the above-identified patent and that said Letters Patent is hereby corrected as shown below:

On the title page: Item [54] Title, delete "KDN-SPECIFIC DEMINONEURAMINIDASE FROM *SPHINGOBACTERIUM MULTIVORUM*" and insert --KDN-SPECIFIC DEAMINONEURAMINIDASE FROM *SPHINGOBACTERIUM MULTIVORUM*--.

Signed and Sealed this

Twenty-fifth Day of May, 1999

Attest:

Q. TODD DICKINSON

*Attesting Officer*    Acting Commissioner of Patents and Trademarks

UNITED STATES PATENT AND TRADEMARK OFFICE
CERTIFICATE OF CORRECTION

PATENT NO. : 5,834,288
DATED : November 10, 1999
INVENTOR(S) : Yasuo Inoue, Sadako Inoue and Ken Kitajima It is certified that error appears in the above-identified patent and that said Letters Patent is hereby corrected as shown below:

On the title page: Item [54] Title, delete "KDN-SPECIFIC DEMINONEURAMINIDASE FROM *SPHINGOBACTERIUM MULTIVORUM*" and insert --KDN-SPECIFIC DEAMINONEURAMINIDASE FROM *SPHINGOBACTERIUM MULTIVORUM*--.

This certificate supersedes Certificate of Correction issued May 25, 1999.

Signed and Sealed this

Thirty-first Day of August, 1999

Attest:

Q. TODD DICKINSON

*Attesting Officer*    *Acting Commissioner of Patents and Trademarks*